(12) United States Patent
McMorrow

(10) Patent No.: US 7,691,136 B2
(45) Date of Patent: Apr. 6, 2010

(54) SYSTEM FOR PROTECTING A COATED MEDICAL IMPLANT

(75) Inventor: David McMorrow, Galway City (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1062 days.

(21) Appl. No.: 10/935,591

(22) Filed: Sep. 8, 2004

(65) Prior Publication Data

US 2005/0049695 A1 Mar. 3, 2005

Related U.S. Application Data

(63) Continuation of application No. 09/954,185, filed on Sep. 18, 2001, now Pat. No. 6,805,703.

(51) Int. Cl.
*A61F 2/82* (2006.01)
*A61F 2/06* (2006.01)

(52) U.S. Cl. .................... 623/1.11; 623/1.46

(58) Field of Classification Search ....... 623/1.11–1.13, 623/1.23, 1.42, 1.46
See application file for complete search history.

(56) References Cited

U.S. PATENT DOCUMENTS

| 5,163,952 | A | * | 11/1992 | Froix | 623/1.18 |
| 5,242,399 | A | * | 9/1993 | Lau et al. | 604/104 |
| 5,634,928 | A | * | 6/1997 | Fischell et al. | 623/1.11 |
| 5,693,066 | A | | 12/1997 | Rupp et al. | |
| 5,800,517 | A | | 9/1998 | Anderson et al. | |
| 5,989,280 | A | | 11/1999 | Euteneuer et al. | |
| 5,992,000 | A | | 11/1999 | Humphrey et al. | |
| 6,063,092 | A | * | 5/2000 | Shin | 606/108 |
| 6,082,990 | A | | 7/2000 | Jackson et al. | |
| 6,096,027 | A | | 8/2000 | Layne | |

FOREIGN PATENT DOCUMENTS

EP 0732087 A1 9/1996
EP 0920843 A1 6/1999

* cited by examiner

*Primary Examiner*—Anhtuan T Nguyen
*Assistant Examiner*—Ryan J Severson
(74) *Attorney, Agent, or Firm*—Kenyon & Kenyon LLP

(57) ABSTRACT

A system for protecting a coated reconfigurable medical implant is provided. This system may include a carrier device having a proximal end and a distal end and a reconfigurable deployable coated medical implant in physical communication with an implant carrying region of the carrier device. In this system the deployable medical implant may be coated with a coating positioned on an exposed surface of the deployable medical implant and the deployable medical implant may be reconfigurable from a first larger configuration to a second contracted configuration. For protecting the coating, the coated medical implant may be encased by a hollow deformable membrane when the deployable medical implant is in the first larger configuration and the membrane may define a cavity with a cross-section that is smaller than the external cross-section of the deployable medical implant. The medical implant may be crimped to its second contracted configuration while the hollow deformable membrane is in place.

12 Claims, 4 Drawing Sheets

1

SYSTEM FOR PROTECTING A COATED MEDICAL IMPLANT

CROSS-REFERENCE TO RELATED APPLICATIONS

This application is a continuation of U.S. patent application Ser. No. 09/954,185 filed Sep. 18, 2001, and entitled PROTECTIVE MEMBRANE FOR RECONFIGURING A WORKPIECE, now U.S. Pat. No. 6,805,703. The entire disclosure of the '185 application is incorporated herein by reference.

FIELD OF THE INVENTION

The present invention regards a system for deploying a coated medical implant. More specifically the present invention regards a system for protecting the coating of a coated medical implant at a time prior to the deployment of the medical implant from a medical device.

BACKGROUND

Articles of manufacture are regularly coated for numerous and varying reasons. For example, they may be coated to protect them from the intrusive handling they can be subjected to during their manufacture and to protect them from the severe environmental conditions they can encounter after they are manufactured. In either circumstance, as well as in others, damage to the coating of a workpiece, resulting from the handling, mishandling or reconfiguration of the workpiece, is an unwanted result.

When the coating of a workpiece becomes scratched or otherwise damaged during its manufacture, the scratches can promote the deterioration of not only the coating but also the workpiece itself by exposing the workpiece's surface to its surroundings. For instance, should the workpiece be employed in a corrosive environment, its errantly exposed surface would be more vulnerable to corrosion than if its coating were completely intact.

Moreover, the scratches and inconsistencies in the coating of a workpiece may also reduce the effectiveness of the finished product. For example, should the coating be used to uniformly deliver some type of releasable substance, inconsistencies in the coating can foster uneven and non-homogeneous delivery of the releasable substance to the deployed product's final surroundings.

An expandable coated stent is one specific example of the coated workpieces described above. Expandable stents are tube-like medical devices designed to support the inner walls of a vessel or lumen within the body of a patient. These stents are typically positioned within a targeted lumen of the body and then expanded to provide internal support for the lumen. These stents may be self-expanding or, alternatively, may require external forces to expand them. In either case they are typically deployed through the use of a catheter of some kind. These catheters typically carry the stents at their distal end.

Due to the interaction of the stent with the inner walls of the lumen, stents have been coated to enhance their effectiveness. These coatings may, among other things, be designed to facilitate the acceptance of the stent into its applied surroundings or to facilitate the delivery of therapeutic to the lumen and its surroundings. When the coating is haphazardly applied or has somehow been removed during the stent's manufacture, both the stent's useable life span and its effectiveness can be reduced.

The coatings on these stent may be applied at various times during its life cycle including during its manufacture, during its placement onto the distal end of the delivery catheter, and contemporaneous with the medical procedure being performed. At each of these times the coating may be at risk of being scratched, damaged or otherwise removed from the surface of the stent. For example, during their manufacture, stents are often crimped onto the distal end of the delivery catheter. During this crimping the mechanical arms of a crimper may come in contact with the coating of the stent as the arms act to reduce the diameter of the stent. This compressive contact can scratch, indent, wipe-off or otherwise breach the integrity of the coating.

SUMMARY OF THE INVENTION

A system for protecting a coated reconfigurable medical implant is provided. This system may include a carrier device having a proximal end and a distal end and a reconfigurable deployable coated medical implant in physical communication with an implant carrying region of the carrier device. In this system the deployable medical implant may be coated with a coating positioned on an exposed surface of the deployable medical implant and the deployable medical implant may be reconfigurable from a first larger configuration to a second contracted configuration. For protecting the coating, the coated medical implant may be encased by a hollow deformable membrane when the deployable medical implant is in the first larger configuration and the membrane may define a cavity with a cross-section that is smaller than the external cross-section of the deployable medical implant. The medical implant may be crimped to its second contracted configuration while the hollow deformable membrane is in place.

DETAILED DESCRIPTION

Figure 1:
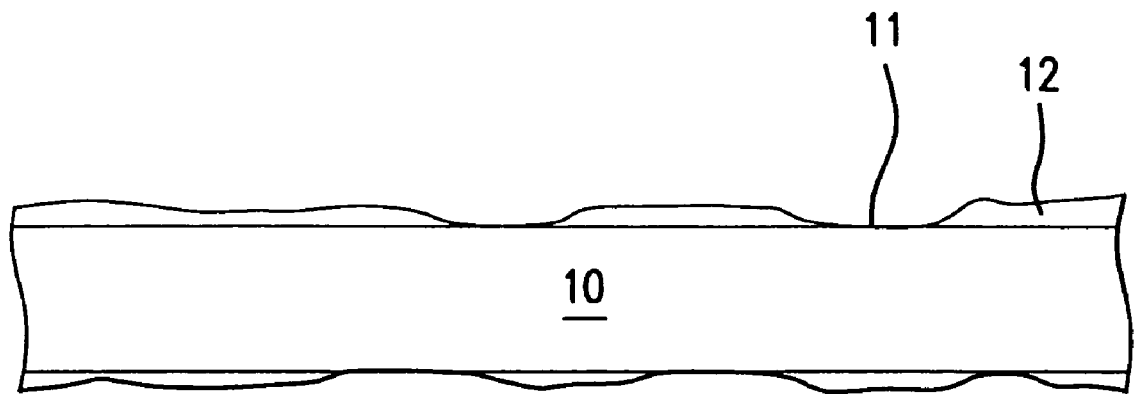
FIG. 1 is a side view of a coated workpiece that was manufactured without a protective membrane in place.

FIG. 1 is a side view of a coated workpiece 10 that was manufactured without the benefit of a protective membrane. As can be seen, the coating 12 of the workpiece haphazardly covers the workpiece 10 and in some areas 11 the workpiece 10 is not covered at all. The missing coating 12 from these removed areas 11 may have been errantly removed during various manufacturing steps and may have even been deposited on both the machinery and the personnel that handled the workpiece during these steps.

Figure 2:
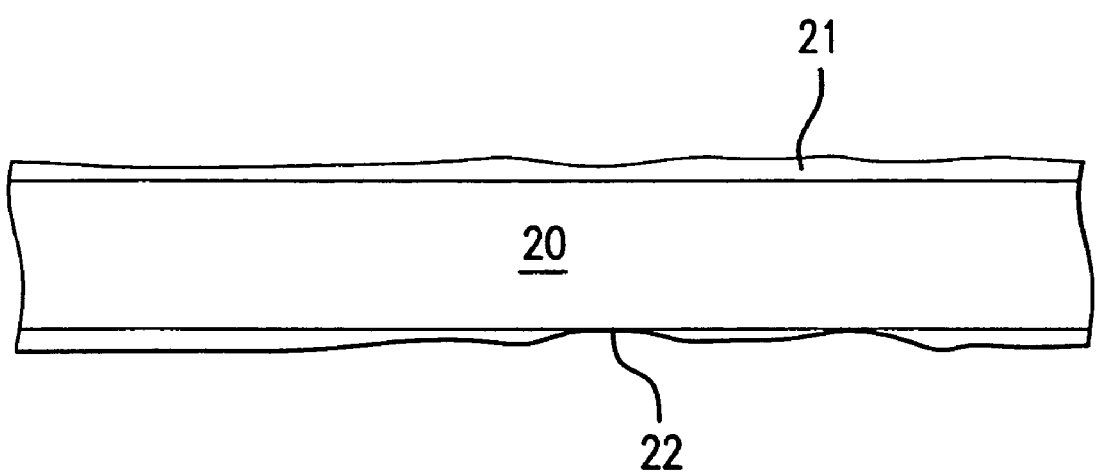
FIG. 2 is a side view of a coated workpiece that was manufactured in accord with an embodiment of the present invention.

FIG. 2 is a side view of a coated workpiece 20 that was manufactured using a protective deformable membrane in accord with one embodiment of the present invention. As can be seen, the workpiece 20 has maintained most, if not all of its protective coating 21 with only a few depressions 22 evident on the workpiece's surface. With more of the coating 21 intact the workpiece 20 may be better suited to perform its desired function after its is deployed for its ultimate use. Moreover, by employing an encasing membrane to protect the coating 21 during the manufacture of the workpiece 20 the loads placed on the workpiece may be more evenly distributed across the coating 21 and the coating 21 may be less susceptible to contaminating everything that comes in contact with it.

Figure 3:
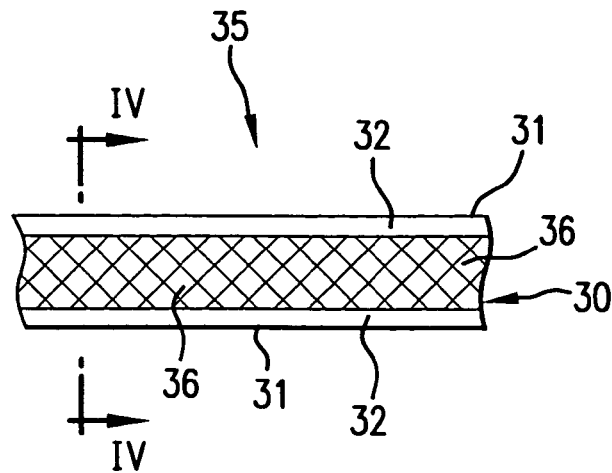
FIG. 3 is a side view of a coated implant that has an encasing hollow deformable membrane surrounding it in accord with an alternative embodiment of the present invention.

FIG. 3 is a side view of a coated implant 35, having a coating 32 that may be protected by an encasing membrane in accord with an alternative embodiment of the present invention. The coated implant 35 in this embodiment, which is comprised of the implant 30 defined by its frame 36, may be covered with a coating 32 that is in turn surrounded by an encasing hollow deformable membrane 31. This encasing deformable membrane 31 may be used to protect the coating 32 during the crimping of the implant 30, during its other manufacturing steps, and during its subsequent handling.

During the crimping of an implant two goals are in conflict, high forces are desired to adequately secure the implant to the implant carrying region of a catheter or other carrier device while reduced forces are desired to prevent the smearing or removal of the coating on the implant 30. By using a protective membrane 31 around the coating the damage caused by the compressive forces necessary to crimp the implant may be reduced. Moreover, by encasing a coated implant in a membrane 31 the smearing or other errant removal of the coating may be diminished by the presence of the membrane 31.

In its resting state the deformable membrane 31 may have an inner diameter that is smaller than the outer diameter of the implant 30. Consequently, the deformable membrane 31 in this embodiment should be enlarged in order to place the coated implant 30 into it. By having the deformable membrane 31 in a state of expansion while it encases the implant 30 the retroactive forces, to return the deformable membrane 31 to its original configuration, can help maintain the positioning of the membrane 31 on the implant 30 during its subsequent handling and use. Alternatively, in a different embodiment, rather than using pure compressive forces to retain the membrane around the implant 30, the deformable membrane may be ribbed or folded or otherwise configured to facilitate its retention onto the implant 30.

Figure 4:
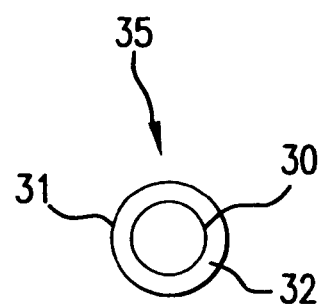
FIG. 4 is a cross-sectional view taken along line IV-IV of FIG. 3.

FIG. 4 is a cross-sectional view taken along line IV-IV of FIG. 3. As can be seen, the encasing hollow deformable membrane 31 of the implant 30 is circular and completely encases the implant 30 and its coating 32. The implant 30 in this configuration has not yet been crimped onto a catheter or other carrier device.

Figure 5:
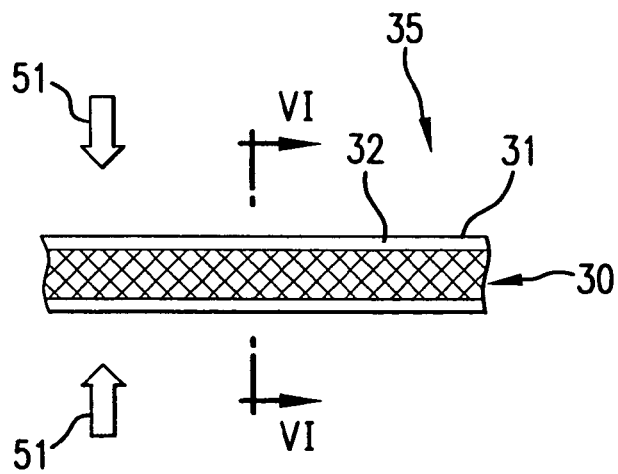
FIG. 5 is a side view of the coated implant of FIG. 3 after it has been reconfigured in accord with an alternative embodiment of the present invention.

FIG. 5 is a side view of the implant 30 after it has been crimped. It is evident in FIG. 5 that the diameter of the implant 30 has been reduced during the crimping process. During this crimping process forces in the direction of arrows 51 have been exerted on the membrane 31 to reduce the diameter of the implant 30. As is evident, the coating 32 has remained intact during this step.

Figure 6:
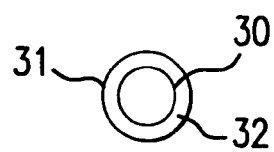
FIG. 6 is a cross-sectional view taken along line VI-VI of FIG. 5.

FIG. 6 is a cross-sectional view taken along line VI-VI of FIG. 5. When FIG. 6 is compared to FIG. 4 the reduction in diameter of the implant 30 is clearly evident.

Figure 7:
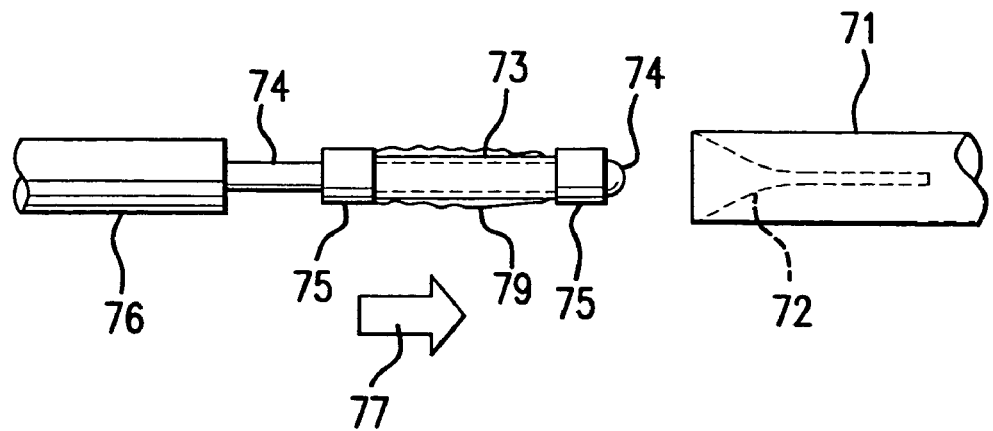
FIG. 7 is a side view of an uncrimped stent on a catheter prior to its insertion into an encasing hollow deformable membrane in accord with another alternative embodiment of the present invention.

FIG. 7 is a side view of a system that may be used in accord with an alternative embodiment of the present invention. In FIG. 7 the carrier device 74 may carry an implant 73 on an implant retention region near its distal end. This implant 73 may be held in place by sox 75 and may be coated with coating 79. The implant 73 and the carrier device 74 may be stored within hypo-tube 76 and may be extended out of the hypo-tube 76 during the manufacturing process, as shown by arrow 77, in order to place the membrane 72 around it. The encasing hollow deformable membrane 72 may be supported or stretched open by one end of an encasing cage 71. This encasing cage 71 may be a wire cage sized to hold the membrane open, it may also be a clear tube or any other device adapted to hold the entrance orifice of the membrane 72 open during the manufacturing process.

During the manufacturing process, the carrier device 74 may be inserted into the entrance orifice of the membrane 72 such that the membrane 72 covers both sox 75 and the implant 73. The membrane 72 may then be slid off of the cage 71 so that the membrane will completely encase the implant and the sox. Then, after the membrane 72 has been slid off of the cage 71, the carrier device may be retracted from the cage 71, now with its implant covered with the protective membrane 72.

Figure 8:
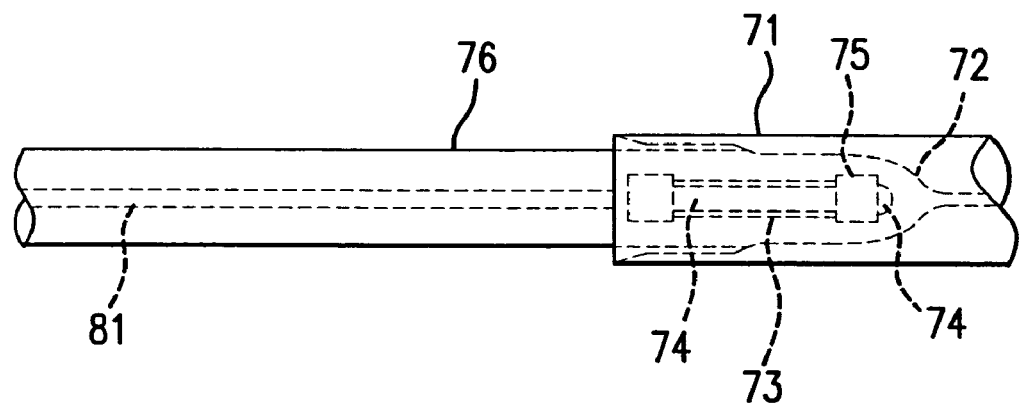
FIG. 8 is a side view of the uncrimped stent of FIG. 7 after it has been inserted into the deformable membrane in accord with another alternative embodiment of the present invention.

FIG. 8 is another side sectional view of the carrier device 74 and the encasing membrane 72 of the embodiment of FIG. 7, this time during the actual covering of the implant 73. In this step, as described above, the hypo-tube 76 has been inserted into the opening of the encasing cage 71 and the encasing hollow deformable membrane 72. Once the hypo-tube has been inserted into this opening a compressed fluid may be injected within a lumen 81 of the hypo-tube in order to inflate the membrane 72. Then, once the membrane is inflated, the distal end of the carrier device 74 may be urged into the membrane 72. The hypo-tube 76 may then be pulled away from the cage 71, stopping the flow of compressed air into the membrane 72 and allowing the membrane to relax and encircle the implant 73. The entrance orifice of the membrane 72 may also be released from the cage 71 at this point to allow the membrane to completely encircle the implant.

Figure 9:
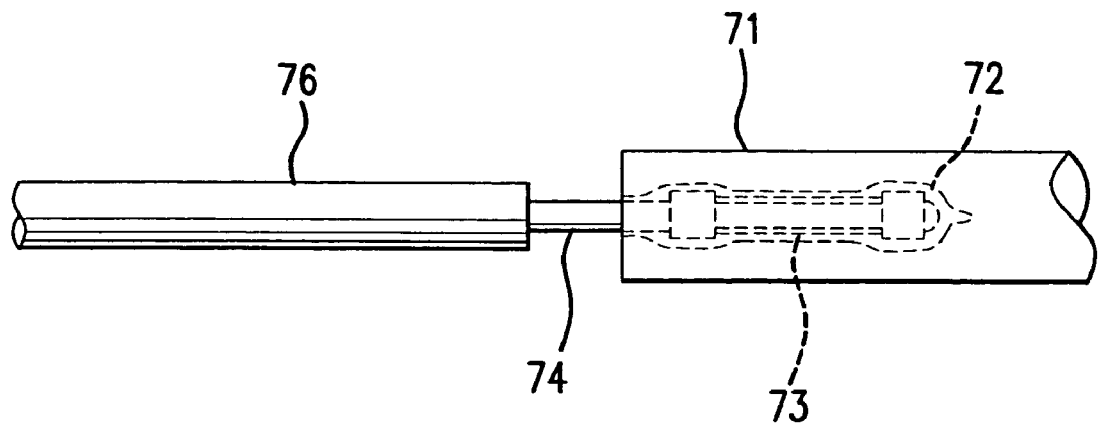
FIG. 9 is a side view of the uncrimped stent of FIGS. 7-8 after the deformable membrane has been placed around it in accord with another alternative embodiment of the present invention.

FIG. 9 shows a side view of the carrier device 74 after the membrane 72 has been released from the cage 71 as described above. As is evident in FIG. 9 the hypotube 76 is no longer inserted into the cage 71 and the implant 73 is now completely covered by the membrane 72. This implant may now be removed from the case 71 and may be processed or handled in subsequent steps with the benefit of the protective membrane.

Figure 10:
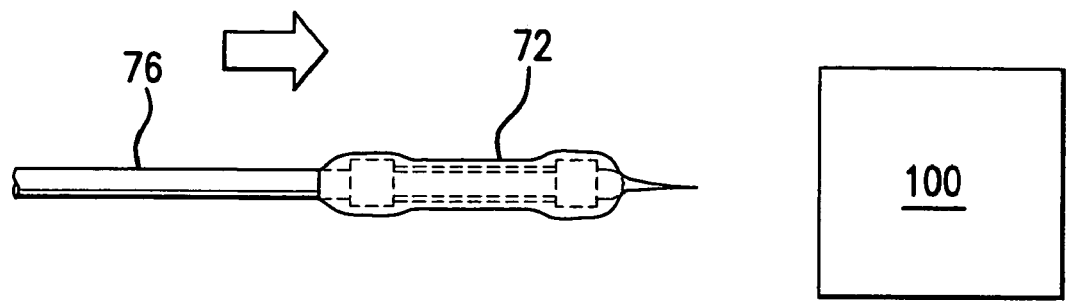
FIG. 10 is a side view of the covered stent of FIGS. 7-9 prior to its insertion into a crimping chamber in accord with another alternative embodiment of the present invention.

FIG. 10 shows a side view of the carrier device of FIGS. 7-9 after the implant has been covered and prior to its insertion into a crimping device 100. This crimping device may be a hand held device or a mechanical device that may reduce the diameter of the implant 73 to more firmly secure it to the implant retention region located at the distal end of the carrier device 76. Once the implant has been crimped, the membrane 72 may be removed immediately or it may remain on the implant 73 until just prior to its use by a practitioner. Alternatively, rather than behaving solely as a crimping mechanism, this device 100 may complete both steps by first applying the membrane and then crimping the implant.

Figure 11:
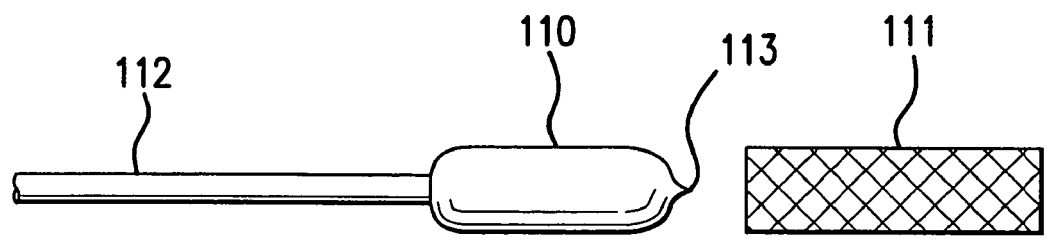
FIG. 11 is a side view of a covered implant prior to its insertion into a braided sleeve in accord with another alternative embodiment of the present invention.

FIG. 11 shows a side view of another alternative embodiment of the present invention. In this alternative embodiment an implant device 112 has an implant covered in a membrane 110 located at the device's 112 distal end. The membrane 110 in this embodiment is shaped like a sleeve and, therefore, has an exit orifice 113. In this embodiment a supplemental cover, here a nylon braided sleeve 111, may be placed over the membrane 110 to further protect the membrane during subsequent manufacturing and handling steps.

Figure 12:
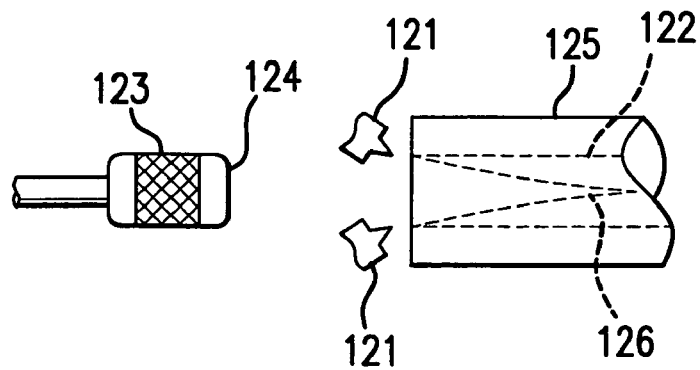
FIG. 12 is a side view of an implant prior to its insertion into an encasing hollow deformable membrane in accord with another alternative embodiment of the present invention.

FIG. 12 is a side view of an implant 123 prior to its insertion into an encasing membrane 126 in accord with another alternative embodiment of the present invention. In this embodiment, rather than having compressed air injected through the hypo-tube, two nozzles 121 are positioned near the cage 125 entrance such that they may inject pressurized fluid into entrance orifice of the membrane 126 stretched open by the cage 125. This cage 125 may also contain a brace 122 within it to prevent the membrane 126 from being over-inflated during the process. Therefore, in use, the membrane may be inflated by the nozzles to allow the implant 123 to be inserted into it. Once the implant has been inserted into the membrane, the membrane may then be slid off of the cage. The carrier device 124, now carrying the implant, may, then, be removed from the cage 125 for subsequent use and handling. Alternatively, rather than injecting fluid to inflate the membrane, the nozzles may be situated behind the membrane and may be used to create a vacuum, thereby drawing the membrane into the cage to enlarge it.

In each of the above embodiments, once the workpiece is ready to be employed for its intended use, or at any other time deemed appropriate by the user, the protective membrane can be removed. The membrane may be removed by inflating or alternatively through some destructive method including a zip cord that will sever the membrane when it is pulled.

A protective membrane as employed in the various embodiments of the present invention can be manufactured from a number of materials, including latex, silicone, polyurethane, chloroprene or nitrile. It may also have a thickness preferably between 0.3 mm and 0.6 mm and contain materials that are flexible and allow for the transmission of forces to the workpiece during the workpiece's manufacture. In one embodiment, the membrane is a tube with a single opening while in another embodiment the membrane is a sleeve with openings on both ends.

The range of medical implants that may be protected by these membranes include: expandable and self-expanding stents, balloon catheters, vena-cava filters, aneurysm coils, stent-grafts, a-v shunts, angio-catheters, and PICC's. Moreover, the coatings employed may contain paclitaxel as well as other therapeutics, which include, for example: pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetylsalicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery medium is formulated as needed to maintain cell function and viability. Modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an antisense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor .alpha. and .beta., platelet-derived endothelial growth factor, platelet-derived growth factor, tumor necrosis factor .alpha., hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

These therapeutic agents can be used, for example, in any application for treating, preventing, or otherwise affecting the course of a disease or tissue or organ dysfunction. For example, the methods of the invention can be used to induce or inhibit angiogenesis, as desired, to prevent or treat restenosis, to treat a cardiomyopathy or other dysfunction of the heart, for treating Parkinson's disease or a stroke or other dysfunction of the brain, for treating cystic fibrosis or other dysfunction of the lung, for treating or inhibiting malignant cell proliferation, for treating any malignancy, and for inducing nerve, blood vessel or tissue regeneration in a particular tissue or organ.

While various embodiments of the present invention are disclosed above other embodiments are also possible without straying from the spirit and scope of the present invention.

What is claimed is:

1. A coated stent in combination with a device for crimping the coated stent and a system for protecting the coated stent during crimping, the combination comprising:
    a catheter, the catheter having a proximal end and a distal end; and
    a stent mounted on the distal end of the catheter, the stent coated with a coating, the coating positioned on an exposed surface of the stent, the stent adapted to be crimped on the catheter from a first configuration wherein the stent has a first diameter to a second configuration wherein the entire stent has a second diameter smaller than the first diameter;
    an encasing hollow deformable membrane, the membrane, in an unexpanded resting state, defining a cavity having a cross-section that is smaller than the external cross-section of the stent when the entire stent is in its second configuration; and
    a device for crimping the coated stent on the catheter from the first configuration to the second configuration;
    wherein the combination has a first positional arrangement while the stent is in the first configuration, wherein in the first positional arrangement the stent is covered by the membrane and is inserted in the crimping device, and wherein the combination has a second positional arrangement after the stent has been crimped to the second configuration, wherein in the second positional arrangement the stent remains covered by the membrane and the stent is no longer inserted in the crimping device; and
    wherein the membrane is adapted to be stretched to an expanded state to facilitate placing the membrane around the stent when the stent is in its first configuration and then released so that the membrane contracts around the stent.

2. The combination of claim 1 further comprising an encasing cage adapted to hold the encasing hollow deformable membrane in the expanded state to facilitate placing the encasing hollow deformable membrane around the stent.

3. The combination of claim 1 further comprising a hypotube adapted to facilitate enlargement of the encasing hollow deformable membrane to the expanded state to facilitate placing the encasing hollow deformable membrane around the stent.

4. The combination of claim 1 further comprising a nozzle adapted to facilitate enlargement of the encasing hollow deformable membrane to the expanded state to facilitate placing the encasing hollow deformable membrane around the stent.

5. The combination of claim 1 wherein the deformable membrane includes a zip cord, the zip cord having an accessible graspable portion extending from the deformable membrane.

6. The combination of claim 1 wherein the deformable membrane has a cylindrically shaped portion.

7. The combination of claim 1 wherein the deformable membrane defines a vessel with a single orifice.

8. The combination of claim 1 wherein the deformable membrane has a thickness substantially between 0.3 mm and 0.6 mm.

9. The combination of claim 1 wherein the catheter is a balloon catheter.

10. The combination of claim 1 wherein the deformable membrane includes an external coating along an outside exposed surface of the deformable membrane.

11. The combination of claim 1 wherein the deformable membrane is covered with a protective covering.

12. The combination of claim 11 wherein the protective covering is a monofilament nylon braided sleeve.

* * * * *